United States Patent [19]

Surka

[11] Patent Number: 4,728,800
[45] Date of Patent: Mar. 1, 1988

[54] APPARATUS AND METHOD FOR DETECTING DEFECTS IN A MOVING WEB

[75] Inventor: Ebun A. Surka, Spartanburg, S.C.

[73] Assignee: Young Engineering, Inc., Spartanburg, S.C.

[21] Appl. No.: 727,284

[22] Filed: Apr. 24, 1985

[51] Int. Cl.[4] ............................................. G01N 21/88
[52] U.S. Cl. .................................... 250/572; 356/238; 356/430
[58] Field of Search ................ 250/572; 356/238, 239, 356/430, 237

[56] References Cited

U.S. PATENT DOCUMENTS 3,589,816  6/1971  Sugaya ........................... 356/238 X
3,694,658  9/1972  Watson et al. .................. 356/237 X Primary Examiner—Eugene R. LaRoche
Assistant Examiner—Robert J. Pascal
Attorney, Agent, or Firm—Dority & Manning

[57] ABSTRACT

Apparatus and method for monitoring a moving web for structural defects at a plurality of independent locations across the width of the web, determining the location and magnitude of a detected defect and controlling movement of the web responsive thereto. A plurality of light sensing elements may be employed operatively connected to a microprocessor. A separate edge sensor may be employed and is claimed.

16 Claims, 7 Drawing Figures

APPARATUS AND METHOD FOR DETECTING DEFECTS IN A MOVING WEB

BACKGROUND OF THE INVENTION

The present invention relates to apparatus and method for detecting defects such as tears, holes or the like in a moving web, such as a textile fabric, evaluating the location and magnitude of the defect and providing control signals responsive thereto.

Webs of material, particularly textile materials such as woven or knitted fabrics are generally characterized as first or second quality goods, depending upon the number of structural or other defects appearing in a predetermined length of the web, and/or the size of the defects. It is obviously significant in the processing of moving textile or other webs that structural defects such as rips, tears, holes or the like, depending upon the location and size of same cannot only create second quality goods, but also can create processing problems. In fact, such defects can worsen during further processing to a point where the web is totally separated and/or to a point where damage to the web becomes adequately great that a process being performed thereon becomes fouled.

Additionally, where long, basically indeterminate lengths of a web, are being joined or batched to provide a continuously operating process, shorter lengths of web are physically sewn together to achieve a large batch. Often the seams are sewn by manual operation of a sewing machine which can lead to faulty seams. In general therefore, webs such as textile material, are fragile to an extent that the web may be cut, slit, torn, or a seam separated, or the like all of which as mentioned above, can lead to a lessening of quality of the goods and thus lower the price of same, or unwanted interruptions of processing equipment such as a finishing range, dyeing range, printing machine or the like.

Hence it is quite important that when a significant length of a textile material is to be fed to a tenter frame, dye range, print machine or the like that the web be free of significant defects both from a standpoint of overall quality and continued operation of the equipment. Furthermore, a particular defect in a moving web may be the product of malfunction of prior process equipment, which if not corrected, may lead to repetitive defects in successive lengths of web being processed thereon.

Furthermore, depending upon a particular type defect in a web, its location and size, one, if knowledgeable of such particular defect may render an independent judgement as to whether the defect is likely to create a problem downstream, will definitely create a problem downstream, or is not likely to create a problem downstream. For example, a very small tear or cut in the selvage of a textile fabric is most likely to continue across the width of the web, thus constituting a type defect that should require immediate attention. Conversely, a moderate but significantly larger cut, tear, rip or the like located in the middle of the web is likely to create a problem downstream only if the defect is significant in size as to endanger the structural integrity of the web, or to present problems to the downstream processing equipment. Upon detection of such a defect, a judgment call needs to be made to ascertain whether the defect can pass or whether the particular processing equipment on which the detector is located should be stopped and the defect corrected, or cut from the moving web followed by a reseaming. Still further, a very small rip or tear at a particular medial location on the web is not likely to create a problem at all, and can perhaps be summarily dismissed without any further judgment and without interruption of the operation of the machine.

Heretofore detection apparatus has been available for determining the existence of a defect in a moving web, and after detection, bringing about stoppage of the process equipment in combination with the actuation of an audible alarm, light or the like to signal to an operator that a defect has been found. At such time, the operator would approach the process equipment and determine what, if any action should be taken with respect to the particular defect, based on his experience. In general such prior defect detectors have included photocells, lasers and the like that are stationarily mounted across the path of a moving web, that themselves move across the path of a moving web, that scan the web, or which are otherwise situated to monitor at least a representative area of the web. Such detectors have, in general, been utilized in conjunction with a dedicated light source to be sensed. In like fashion, other electronic sensors have been utilized for defect detection.

Heretofore, defect detectors, as noted above, have not eliminated the need for an individual to remain at the inspection site for a majority of the time, but have primarily been utilized to eliminate the need for an inspector or inspectors as the case may be, to physically view the entire web as it passes through an inspection station. In fact, for high tech end uses, or other fabrics where the quality of same is critical, it is still a general rule rather than an exception, that one or more operators physically man an inspection station and view the entirety of a length of web being processed.

The present invention is addressed to the same type problems as prior art detectors, though from a standpoint of operation and efficiency overcomes problems noted above. In fact, the present invention achieves not only correct detection of both location and magnitude of a defect, but also can control web process equipment responsive thereto. There is no known prior art that is believed to anticipate or suggest the subject matter of the present invention.

SUMMARY OF THE INVENTION

It is an object of the present invention to provide an improved apparatus for the detection of structural defects in a moving web such as a textile fabric.

Another object of the present invention is to provide an improved apparatus that may be located across the width of a moving web of virtually any dimension to constantly monitor the entire width of the web for structural or discontinuity type defects such as rips, tears, holes and the like.

Yet another object of the present invention is to provide improved apparatus for the detection of structural defects in a moving web and determination from the detection the location and magnitude of the defect.

Still further another object of the present invention is to provide an apparatus for detecting structural defects in a moving web, such as a textile material, where the defect is categorized by location and size by the input of individual signals from individual detection devices to a programmed control means where, depending upon the particular detectors activated, the control means permits the defect to pass, automatically shuts the machine down, or interrupts operation of the machine to permit an operator to make an independent judgment with respect to the defect.

Still another object of the present invention is to provide an improved method for the detection of structural defects in a moving web and to ascertain from the detection the size and magnitude of the defect.

Yet another object of the present invention is to provide an improved method for determining the existence of structural defects such as holes, rips, tears and the like in a moving web, for determining the location and magnitude of the detected defect, and to control operation of the web handling machine responsive to the detected defect.

Generally speaking, apparatus according to the present invention for detecting structural or discontinuity defects in a moving web comprises a plurality of light sensitive elements located across an intended path of travel for the web with the web being movable thereby between said elements and a source of light, said elements being actuatable by light from said source passing through a discontinuity defect in said web, said elements having a predetermined spacing therebetween and monitoring substantially the full width of the web, and control means operatively associated with said elements to determine the location and magnitude of detected discontinuities in said web from the particular elements actuated by light passing through said discontinuity, and control movement of said web responsive thereto.

More particularly, in a preferred embodiment, apparatus according to the present invention not only includes a series of light sensitive elements that are physically located to monitor substantially the entire width of a web passing thereby, but additionaly includes a further, related apparatus that makes physical engagement with opposite edges of a web passing thereby to detect rips, tears, holes or other defects in an edge of the web, which detection apparatus is likewise operatively associated with the control apparatus for the web handling equipment whereby the mode of operation of the equipment will be dictated by presence or absence of defects in the web.

In a particular industry such as the textile industry, it is generally known from experience that one particular type and/or size defect at a particular location in a fabric is more damaging to the fabric than another. Consequently, various types and magnitudes of defects have been categorized and incorporated into a computer program such that when an individual detector element is actuated and provides input to the control means, preferably a microprocessor, location of the defect can be determined by the particular element actuated with the size of same also determined by the number of contiguous elements actuated. Such information may be compared to the programmed categories of defects, and depending upon the particular comparisons, the web handling equipment will continue to run, stop, or be interrupted for human judgment as to whether the defect may or may not be critical.

The sensitive elements are preferably located in modular housing units of a particular length. A plurality of module containing light sensitive elements may thus be located across the path of the web in side-by-side fashion to totally monitor a web of any particular width. Alternatively, one such housing may contain all of the detector elements. In deployment of individual modules of light sensitive elements, adjacent modules are generally offset from one another along the path of web travel so that void spaces between the modules will not occur.

In like fashion, the edge or selvage of a web, depending upon the type of web being monitored is normally critical whereby a very small rip or tear in the web edge will likely extend fully across the web during further handling, or if not totally thereacross, certainly to an opposite edge or selvage. Accordingly, in a preferred embodiment a second, related structure is utilized solely for monitoring an edge or selvage of the web, making biased contact therewith. Upon detection of a discontinuity in the edge, an element biased into contact with the web will move out of its normal position, and thereby actuate a sensor operatively associated with the control means to provide input of a defect to the control means.

Generally speaking, the method of detecting defects according to teachings of the present invention, comprises the steps of monitoring a web at a plurality of predetermined independent locations across the width of same; providing input to a control means from each independent location where a defect is detected, determining location and magnitude of said detected defect from the particular location inputs; and controlling movement of the web dependant upon location and magnitude of a detected defect.

More specifically, in a preferred method of the present invention, a light source and a plurality of individual light sensitive elements are pre-arranged to monitor the full width of a web passing thereby. Structural defects in the web permit light passage therethrough which actuates one or more of the light sensitive elements depending upon the size of the defect. Output from the individual light sensitive elements collectively determines location and magnitude of a defect detected which is compared to predetermined defect categories and movement of the web is controlled dependant upon said comparison.

Still further in a most preferred arrangement of the present invention, a separate but related detector is located along each edge of a web path with a portion of same being biasable into contact with a web passing thereby, and being movable to an opposite surface of the web upon contact with an edge defect. Conseqent actuation of an input providing means operation of the web handling means.

BRIEF DESCRIPTION OF THE DRAWINGS

The construction designed to carry out the invention will be hereinafter described, together with other features thereof.

The invention will be more readily understood from a reading of the following specification and by reference to the accompanying drawings forming a part thereof, wherein an example of the invention is shown and wherein.

DESCRIPTION OF THE PREFERRED EMBODIMENTS

Figure 1:
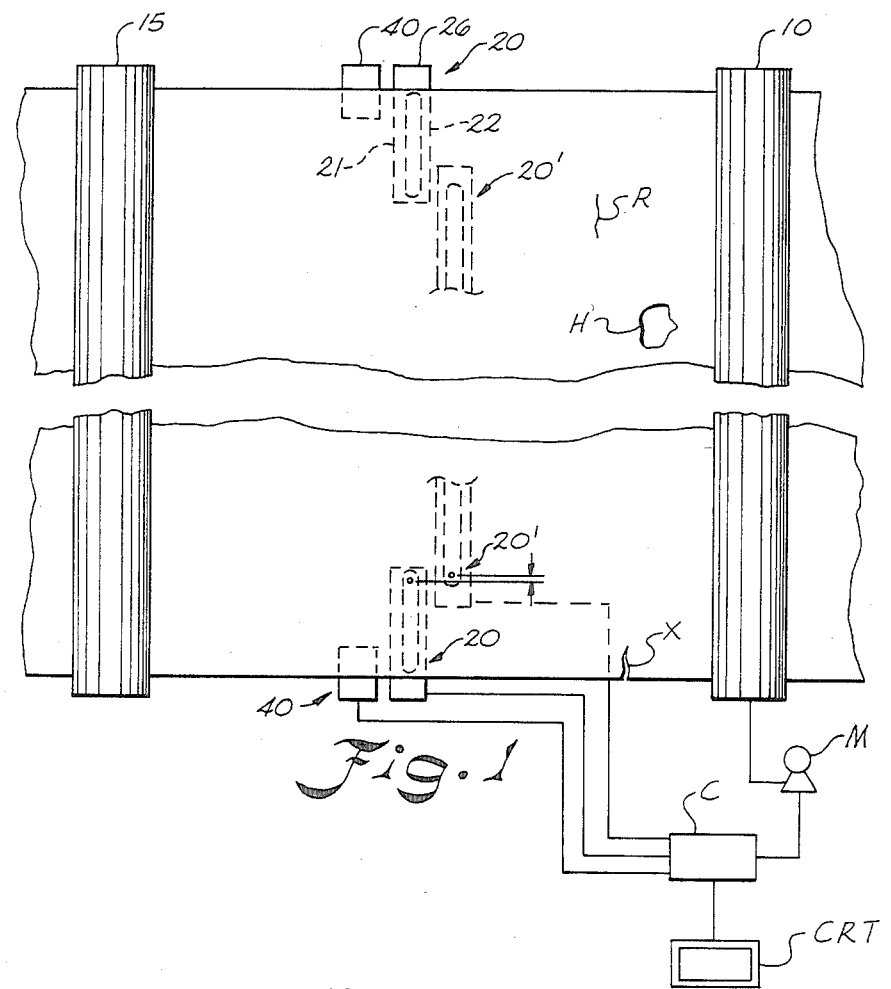
FIG. 1 is a plan schematic view of preferred detection apparatus according to the present invention located along a path of travel for a web to be monitored, and with a web passing thereover.

Making reference to the Figures, preferred embodiments of the present invention will now be described in detail. FIG. 1 schematically illustrates one arrangement for apparatus of the present invention in which a web W is being forwarded by drive means indicated by rolls 10 and 15 having drive power supplied thereto by a motor M or the like. Web W follows a path of travel as indicated by the arrow and passes adjacent defect detecting units generally indicated as 20, 20' and 40. As illustrated, defect detector units 20, 20' are modular units containing light sensitive elements generally 30, with a predetermined center-to-center spacing. Individual modules 20, 20' are offsetable with respect to the direction of travel of the web such that an indeterminate number of modules 20, 20' may be deployed across the path of travel of a web of virtually any width. An edge defect detector unit generally 40 may also be located at opposite edges of web W in a preferred embodiment to specifically monitor web W for defects in the edge or selvage. As schematically illustrated in FIG. 1, defect detector units 20, 20' and 40 are each operatively associated with a control unit C, which in a preferred embodiment is a microprocessor, further details of which will be described hereinafter.

Detector units 20, 20' are each generally identical in structure and in a modular concept are preferably a predetermined length and contain like numbers of light sensitive elements 30. Such modular units may be staggered as illustrated whereby a constant predetermined distance between individual sensing elements is maintained across the entire width of the fabric for total monitoring of same.

With a plurality of individual sensing elements 30 located across the width of a path of travel of a web, and with each individual sensing element 30 operatively associated with a control means C such as a microprocessor, both location and magnitude of a particular defect may be ascertained by the specific sensing elements actuated. Note for example in FIG. 1 a rip R has been symbolically illustrated in web W. When rip R passes over module 20' particular individual sensing elements 30 along the length of rip R will receive ambient light from above web W and be actuated thereby. Particular actuated elements 30 are determined by control means C.

In similar fashion, a hole H has been indicated in web W which likewise permits a predetermined number of individual sensing elements 30 spanning the width of hole H to be actuated by ambient light from above and to remain actuated until hole H passes beyond same. Consequently, actuated elements 30 provide input to control means C again as to location and magnitude of the defect. In this case, however, both length and width of the hole are determined. Still further, a cut X illustrated in web W along an edge of same which when passing over edge detector 40, will cause detector 40 to become actuated as will be described hereinafter. Actuation of detector 40 will then be inputted to control means C, again to indicate location of cut X as being in the edge of the web.

In the fashion noted above, the apparatus of the present invention is capable of monitoring one hundred percent of a web W passing thereover. As mentioned hereinbefore, handling of a web W having defects therein is dependant not only upon the location of the defect, but also the size of same as to whether it is necessary for the defect to be repaired, to be removed from the web, or where, under ordinary circumstances the defect will not create a downstream problem in the web and can be permitted to pass on.

In a most preferred arrangement according to the present invention, the existence of such type defects are programmed into a microprocessor so that when a particular defect is detected by sensing elements 30 and inputted to the microprocessor, location and magnitude of such defect is compared to programmed defect conditions and the microprocessor thereafter renders appropriate controlled output signals to a motor M for continued movement of web W, for stoppage of movement of web W, or for interruption of movement of web W to permit an operator to make an independent judgment as to the effect of a particular defect. Output from microprocessor C could additionally actuate an alarm means such as an audible or visual signal to indicate stoppage of the movement of the web, or the like.

Still further, in another embodiment of the present invention, microprocessor C may be programmed such that actual location and magnitude of a defect being detected may be graphically displayed on a cathode ray tube CRT. Cathode ray tube CRT, for example, could be positioned in a management office where based on visual observation of a graphic presentation of a defect, a determination could be made at the management office, remote from the machine as to whether the defect is critical to continued operation.

Moreover, continuous printout of web defects as well as continuous inputting of the defects into memory could serve as a log of the particular web being handled. Such a log could thereafter be utilized by management for one of a number of reasons. For example, the actual log of defects could be compared to downstream performance of the web and thereafter be used for upgrading comparative defects utilized to determine the need or desirability for corrective action. Likewise, should a particular defect repetitively appear in the log, such would indicate the need for corrective action in an upstream process or for upstream process equipment.

All-in-all, utilization of a system according to the present invention will not only lead to improved web quality, and improved operation of downstream process equipment, but also will serve as a very valuable management tool.

Preferred embodiments of instant defect detectors will now be described. Making reference to FIGS. 2 and 3, a portion of a module housing 20 is illustrated having a top wall 21, side walls 22, 23 a bottom wall 24 and end walls 25 and 26 (26 not shown). Module 20 is provided with a slot 27 in a top wall 21 of same with a slit 28 located at a lower end of slot 27. Likewise, beneath slit 28, housing 20 is hollowed out to define a cavity 29 for receipt of operative elements of the detector system.

Notably, a plurality of light sensing elements 30 are received in an appropriate cavity 21 beneath slit 28 to receive light from above. Light from a source extends through slot 27 and slot 28 for actuation of light sensing elements 30.

A series of light sensing elements 30 located along the length of slit 28 with a predetermined spacing therebetween are mounted on a circuit board 32, and are operatively associated therewith. Output from the individual light sensing elements 30 may be transmitted to the control means C in the fashion noted above.

Figure 3:
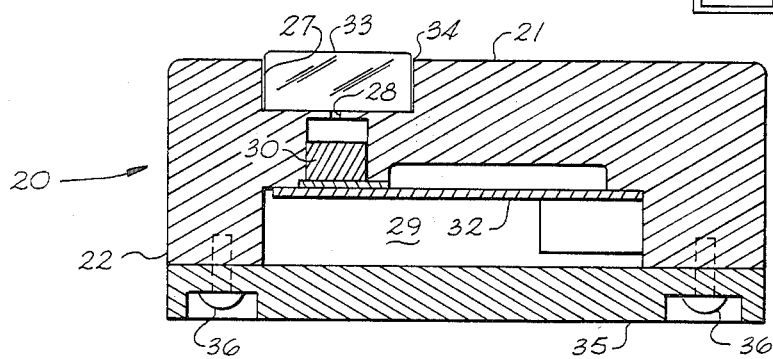
FIG. 3 is a vertical cross-sectional view through the housing of FIG. 2 taken alone a line III—III.

As illustrated, particularly in FIG. 3, a transparent plate or panel 33 is received within slot 27 with an appropriate sealant 34 received around the periphery of same to preclude dust and other debris from passing thereby. Transparent panel 33 extends above top wall 21, with a web being monitored making contact therewith, whereby panel 33 remains free of dust, lint or the like which could adversely affect light transmission therethrough. In like fashion, a bottom cover plate 35 is provided for housing 20 and secured thereto with bolts 36 or the like to close housing 20 against ingress of dust, debris and the like, while at the same time permitting ease of fabrication, repair and/or replacement of circuit boards and light sensitive elements in the event such should be desired or required. In a preferred situation, transparent panel 33 is glass, plexiglass or the like, and with the size of transparent panel 33 being coincident with the size of slot 27 which of course is wider than slit 28, light may be permitted to enter slit 28 from a wide angle as opposed to a direct overhead arrangement.

Figure 2:
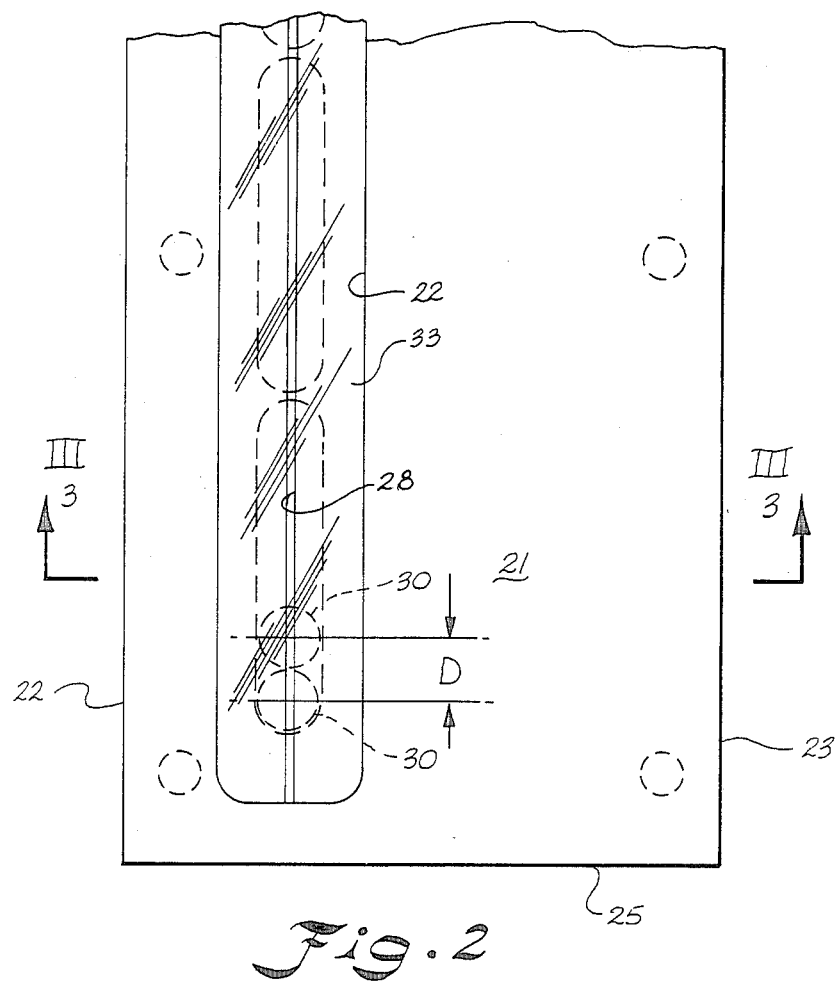
FIG. 2 is a top plan view of a housing for light sensitive detector elements according to teachings of the present invention.

As is seen in FIG. 2, a pair of light sensing elements 30 are illustrated beneath slit 28 being located at a predetermined center-to-center spacing D. Other light sensing elements 30 would also have a same center-to-center spacing, with adjacent modules 20 being offset such that a same center-to-center spacing may exist between an end light sensing element 30 of one module 20 and an adjacent end light sensing element 30 of an adjacent module 20'. Still further, if necessary or desirable to improve the degree of coverage of the full width of the web being monitored, individual light sensing elements 30 within a single module could likewise be offset, one with respect to the other to ensure total overlap of coverage across the full width of the web.

Figure 4:
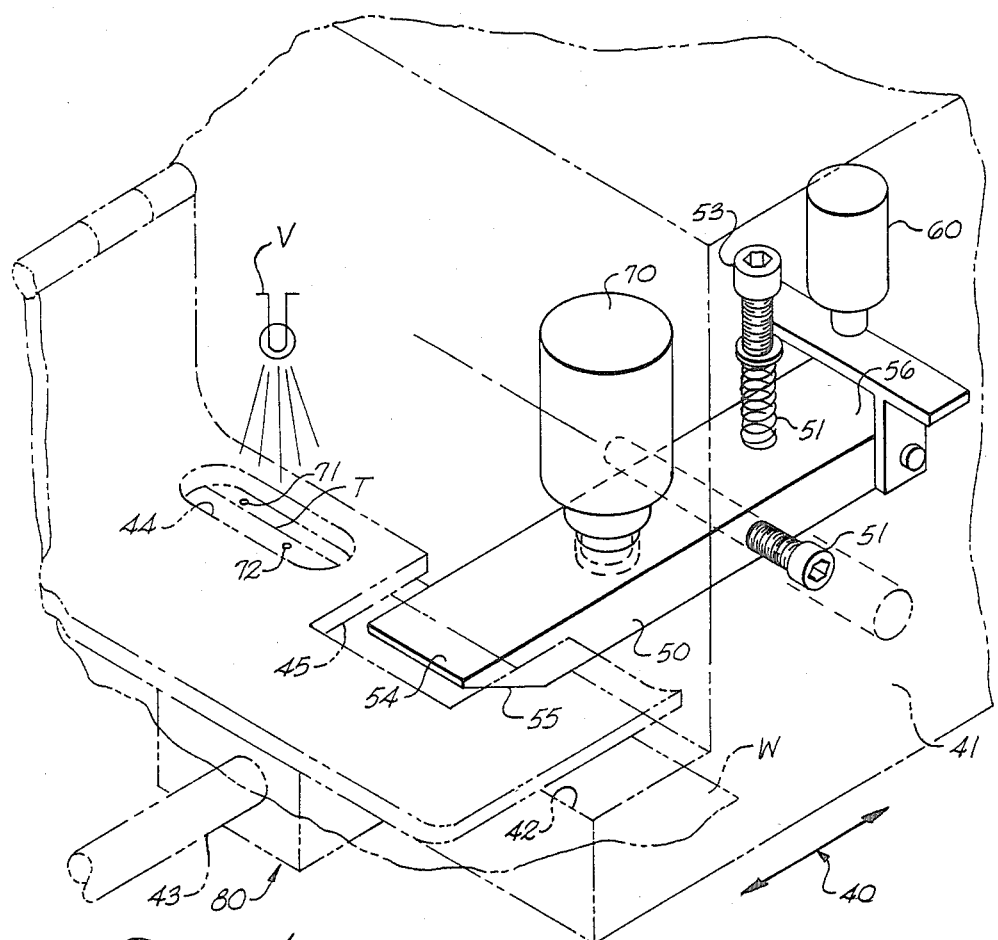
FIG. 4 is a partial isometric view of a web edge defect detection device as illustrated in FIG. 1 with exterior portions of same being illustrated in phantom for more ready illustration of operative components of same.

Referring to FIGS. 1 and 4, an edge detector device generally indicated as 40 will be described. Detector 40 includes a housing 41 within which the operative elements of the detector are received. Exterior of housing 41 is a ledge 42 having a cover plate 43 pivotally secured to housing 41 and locatable over ledge 42. Cover plate 43 defines an opening 44 therewithin through which position of a web passing thereunder may be ascertained. Cover plate 43 further defines an opening 45 therein for purposes of defect detection as will be described immediately hereinafter. Ledge 42 of housing 41 includes a pair of light sensing elements 71 and 72 that are spaced apart to define a web edge path therebetween. Furthermore, housing 41 is mounted adjacent the edge of the web path of travel on an appropriate adjustment means generally 80 that is operatively associated with output from light sensing elements 71 and 72.

With a web W passing between cover plate 43 and ledge 42, a terminal edge of same should pass between light sensing elements 71 and 72, indicating correct positioning. In the event, however, the terminal edge T of web W moves away in either direction from the space between elements 71 and 72, adjustment means 80 will make appropriate correction to housing 40 to reposition the terminal edge T of web W between the light sensing elements 71 and 72. Particularly, as illustrated in FIG. 4, should terminal edge T of web W cover light sensing element 71, adjustment means 80 will move detector 40 away from web path of travel whereas should light sensing means 72 become uncovered, the reverse correction would occur. In this fashion, the terminal edge T of web W is maintained in a proper location for monitor by detector means 40.

A sensing lever 50 is received within housing 41 of detector 40 for pivotal movement about a pivot point defined by a mounting screw 51 or other means for securing lever 50 to housing 41. A spring or other biasing means 52 is located behind pivot point 51 and applies a downward force which is adjustable by means of a set screw 53 to provide an upward bias at an outer terminal end 54 of lever 50, against an underside of a web W passing thereover. Outer free end 54 of lever 50 is provided with a beveled surface 55 along an underside of same for a purpose to be described hereinafter. An optical switch 60 or other sensing means is mounted above a rear end 56 of lever 50 and is operatively associated with control means C such that should a defect occur in the terminal edge T of web W, a forward edge 54 of lever 50 will move upwardly therethrough about pivot point 51. Rear end 56 of lever 50 thus moves downwardly away from optical switch 60, actuating switch 60 which provides input to control means C to indicate the presence of a defect. In order to reset lever 50 for further detection, a solenoid 70 or the like is provided above a portion of lever 50 forward of pivot point 51, and is operatively associated with switch 60 such that upon actuation of switch 60, solenoid 70 is likewise actuated to contact lever 50 forcing forward end 54 of same downwardly. Beveled portion 55 of lever 50 engages web W, forces same out of the way and permits a return of forward end 54 of lever 50 beneath web W.

In a proper orientation, lever 50 is maintained level beneath the surface of web W with web W being held down against lever 50 by cover plate 43. Cover plate 43 thus prevents web W from flapping at high speed operation, while also applying a counterforce to spring 52 and maintains lever 50 in a level position so long as the edge T of web W contains no defects. Likewise as shown in FIG. 4, a light source L is schematically depicted above cover plate opening 44 and may be used for both light sensors 71 and 72 for maintaining detector 40 in a proper disposition with respect to the edge of the web.

Figure 5:
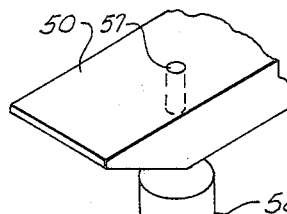
FIGS. 5, 5A and 5B are partial illustrations of an edge detector device according to the present invention showing a further embodiment of same.
Figure 5A:
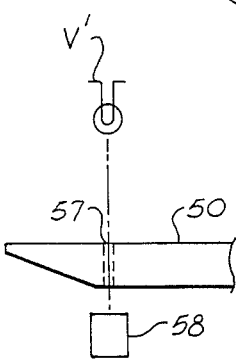
Figure 5B:
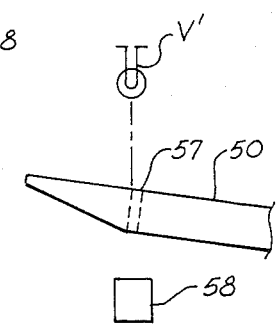

A further embodiment of the present invention is illustrated in FIGS. 5, 5A and 5B, which in essence obviates the need for the optical switch 60 that was described with respect to FIG. 4. In the embodiment as shown in FIGS. 5, 5A and 5B, an opening 57 is provided in a forward end of lever 50 with a light sensing element 58 locatable beneath lever 50, in alignment with opening 57. A light source L' is locatable above opening 57 and is arranged to provide light to sensor 58 through opening 57 when lever 50 is in a level position as illustrated in FIG. 5A. If, however, a defect occurs in the edge of web W and lever 50 moves upwardly therethrough, opening 57 moves out of alignment with light source L' which precludes light from reaching sensor 58 whereby output from sensor 58 would thus provide input to control means C that a defect had occurred. In like fashion sensor 58 would actuate solenoid 70 or other resetting means to return lever 50 to its operative level position.

While the preferred arrangement of detector means according to the present invention have been set forth and described above, the modules containing the plurality of light sensor elements could in fact be utilized separately from the edge defect detector, and likewise the edge defect detector could be utilized separately from the modules. Furthermore, while as set forth herein, the light sensing elements have been generically mentioned, obviously photocells, phototransistors or the like may be employed. Still further, while one advantage of the system of the present invention is the ability to utilize ambient fluorescent or other type light in conjunction with the light sensing elements, obviously if necessary depending upon the environment in which the unit is to be employed a dedicated light source may be provided.

It will be understood, of course, that while the form of the invention herein shown and described constitutes a preferred embodiment of the invention, it is not intended to illustrate all possible forms of the invention. It will also be understood that the words used are words of description rather than of limitation and that various changes may be made without departing from the spirit and scope of the invention herein disclosed.

What is claimed is:

1. Apparatus for detecting discontinuity defects in a moving web comprising a plurality of light sensitive elements located across an intended path of travel for said web with said web being passable thereby between said elements and a source of light, said elements being actuatable by light from said source passing through a discontinuity defect in said web, said elements having a predetermined width and a predetermined spacing therebetween and monitoring substantially the full width of the web, and a programmable controller operatively associated with said elements to receive input therefrom when said elements are actuated by light passing through a discontinuity in said web, to determine the location and magnitude of a discontinuity in said web responsive to said input, to compare said input to preprogrammed defect data, and to control web movement dependent upon said comparison so that web stoppage is achieved only for those detected defects whose location, magnitude, or combined location and magnitude dictate same.

2. Apparatus as defined in claim 1 wherein a predetermined number of said elements are received in a housing of a module, and wherein a plurality of said modules are located across said path of travel, each adjacent module being offset so that end elements of adjacent modules are spaced apart by like amounts to elements within one of said modules.

3. Apparatus as defined in claim 2 wherein said housing defines a groove in an outer wall said groove defining a slot in a bottom of same, said slot being lesser in width than said groove, and wherein said elements are located below said slot.

4. Apparatus as defined in claim 3 wherein a transparent cover is secured within said groove and sealed therearound.

5. Apparatus as defined in claim 4 wherein said elements are received on a printed circuit board and are secured within said housing.

6. Apparatus as defined in claim 1 comprising further discontinuity defect edge detector means located along opposite edges of said web, said edge detector means having means thereon engageable with said web edge and being biased thereagainst, said biased engagement means being movable to an opposite side of said web when an opening in a web passes thereby, said edge detector means being operatively associated with said control means.

7. Apparatus as defined in claim 6 wherein said edge defect detector means has edge sensing means associated therewith, said sensing means maintaining said detector means at said edge.

8. Apparatus as defined in claim 7 wherein said biased engagement means is adjustable and having means associated therewith to automatically return said engagement means to an opposite side of said web after detection of a defect.

9. Apparatus as defined in claim 8 wherein said edge detector defines an edge passageway therethrough.

10. Apparatus for detecting separation defects in a moving web comprising:
    (a) a plurality of light sensitive elements located along a web path with a web being passable thereby between said elements and a source of light, said elements having a predetermined spacing therebetween and monitoring substantially the entire width of said web between opposite edges of same,
    (b) programmed control means operatively associated with said elements and operatively associable with means for moving said web, said control means being preprogrammed for different control outputs dependent upon the locations and sizes of detected defects, receiving input from elements actuated by light passing through a defect in said web, comparing said input to said preprogrammed data and providing control output dependend thereon; and
    (c) web edge separation detector means operatively associated with said control means, said edge detector means comprising means biased into engagement with a surface of said edge and being movable to an opposite surface of said edge upon detecting a separation in said edge, said control means providing web control output upon detection of an edge separation.

11. Apparatus as defined in claim 10 wherein said web engagement means is biasable into engagement with an underside of said web edge, and further includes means to return said engagement means to a position beneath said edge after said engagement means moves through a defect above said web.

12. Apparatus as defined in claim 10 comprising further sensing means associated with said edge detector to continually sense said web edge and maintain said detector thereat.

13. Apparatus as defined in claim 10 wherein said edge detector engagement means comprises a pivotal lever, said lever being spring biased about said pivot point, said lever having means associated therewith to sense movement of said lever responsive to detection of a defect, said sensing means being operatively associated with said control means, and lever reset means associated with said sensing means to return said lever to a detecting position after a defect is detected.

14. Apparatus as defined in claim 13 wherein said edge defect detector further comprises means to engage a web on a surface opposite said lever so that said web is maintained at said lever during movement.

15. A method of detecting discontinuity defects in a moving web, comprising the steps of:
    (a) monitoring said web as it moves past a plurality of predetermined, independent locations spaced at substantially equal distances across the width of said web;

(b) programming a control means with data for different control outputs dependent upon the location and sizes of possible defects;

(c) generating a data signal from each of said locations when a defect is detected while monitoring said web;

(d) transmitting said signals to said control means;

(e) comparing data received from said signals with said programmed data to determine the location and size of said detected defects; and (f) controlling movement of said web dependent upon the location and/or size of said detected defects.

16. A method of detecting discontinuity defects in a moving web, comprising the steps of:

(a) monitoring said web as it moves past a plurality of predetermined spaced independent locations acorss the width of said web;

(b) programming a control means with data relating to known defects and expected consequences therefrom;

(c) generating data relating to the magnitude and location of detected defects;

(d) comparing said data generated from detected defects with data relating to said known defects and consequences; and (e) controlling further movement of said web in response to output signals resulting from said comparison.

* * * * *